United States Patent [19]

Le Coq et al.

[11] Patent Number: 4,539,639

[45] Date of Patent: Sep. 3, 1985

[54] PROCESS FOR OBTAINING THREE-DIMENSIONAL IMAGES OF AN OBJECT AND ITS APPLICATION TO THE TOMOGRAPHY OF AN ORGAN

[75] Inventors: Gérard Le Coq, Fesnes; Françoise Soussaline, Paris, both of France

[73] Assignee: Commissariat a l'Energie Atomique, Paris, France

[21] Appl. No.: 463,811

[22] Filed: Feb. 4, 1983

[30] Foreign Application Priority Data

Feb. 17, 1982 [FR] France ................................ 82 02632

[51] Int. Cl.³ .............................................. G06F 15/42
[52] U.S. Cl. ................................ 364/414; 250/363 S; 378/901
[58] Field of Search ..................... 364/414; 250/363 S; 378/901

[56] References Cited

U.S. PATENT DOCUMENTS 4,213,054  7/1980  Doherty, III ................ 250/363 S X
4,281,382  7/1981  Knoll et al. ......................... 364/414

FOREIGN PATENT DOCUMENTS 2026280  1/1980  United Kingdom ........ 250/363 S X Primary Examiner—Jerry Smith
Assistant Examiner—Lonis Woo
Attorney, Agent, or Firm—Oblon, Fisher, Spivak, McClelland & Maier

[57] ABSTRACT

A process and apppparatus for obtaining three-dimensional images of an object with an application of the process and the device to the tomography of an organ. The device includes a detector or mobile rays which rotates about the object and mechanisms which provide references for the angular position of the detector with respect to the reference plane. The detector contains detection areas which receive the radiation and are identified by their number and emit signals, the amplitude of which depends on the intensity of the received rays. Also included in the device is an iterative processing machine which operates by convergent processing of the signal amplitude values with the processing mechanism being connecting to visualization devices in order to display the images of the object in various cross-section planes after each iteration.

9 Claims, 8 Drawing Figures

PROCESS FOR OBTAINING THREE-DIMENSIONAL IMAGES OF AN OBJECT AND ITS APPLICATION TO THE TOMOGRAPHY OF AN ORGAN

BACKGROUND OF THE INVENTION

1. Field of the Invention

The present invention relates to a process for obtaining three-dimensional images of an object, as well as the application of this process to the tomography of an organ. It more particularly applies to the reconstruction of three-dimensional images to an organ in the human body, on the basis of the detection of gamma radiation from a tracer injected into the organ. It can also be used in the reconstruction of three-dimensional images from the detection of radiation from an object or an organ.

2. Description of the Prior Art

It is known to restore the radioactive distribution of a three-dimensional object, in accordance with a succession of planes having random orientations relative to said object. The acquisition of the initial data is based on the measurement, with the aid of a scintillation camera or scintiscanner, which is sensitive e.g. to gamma radiation, of photons emitted by a radioactive tracer injected into the organ or object, which it is desired to examine. This measurement is carried out during a 360° rotation of the camera about a major axis of the organ or object, which it is desired to examine. For each of the camera rotation angles about the object or organ, a so-called scintigraphic image thereof is obtained. In general, the camera used is a scintillation camera, whose collimator is constituted by a lead plate having a large number of cylindrical or hexagonal holes with parallel axes, giving access to a radiation detector, a group of collimator holes facing an elementary detection zone supplying a detection signal in the presence of radiation. This collimator makes it possible to eliminate photons, which are emitted in directions not perpendicular to the plane of the detector. The scintigraphic image obtained results from the sum of the photons from the elementary cells of the organ or object, which emit radiation in directions perpendicular to the plane of the camera and which are therefore parallel to the collimator channels. The elementary cells are aligned in these directions. Thus, the obtaining of each scintigraphic image for each position of the camera, results from radiation emitted by elementary emitting cells located on straight lines perpendicular to the plane of the camera. For each of the angular positions of the camera about the organ to be examined, the electrical signals from the detector are proportional to the number of photons received in directions perpendicular to the camera plane. As a function of the different elementary detection zones, these electrical signals are digitized and recorded in an e.g. magnetic memory for use in the reconstruction of images of the organ to be examined, for the different angular positions of the plane of the detectors relative to the organ or object to be examined.

The digitized signals recorded in the memory are sorted as a function of each angular position of the plane of the detectors about the organ, for a rotation of 360° of the said plane. The digital values are processed by a special algorithm, so as to restore the radioactive distribution of the tracer contained in the organ or object, in accordance with a so-called "reconstruction" method. In order to obtain sectional images for different sectional planes perpendicular to the detector plane, every effort is normally made to perform a minimum number of processing operations on the signals from the detector, using a minicomputer, without precisely taking into account the physical limitations limited with the radiation detection system, i.e. the limitations associated with the camera. In addition, no account is taken of the effect of autoabsorption of the radiation within the organ or object to be examined. All these approximations are prejudicial to the quality of the images obtained. For the energy of the gamma radiation currently used in nuclear medicine, this autoabsorption phenomenon is the most serious cause of the deterioration of quantitative data having to be processed in order to obtain a correct image of the body to be examined.

BRIEF SUMMARY OF THE INVENTION

The problem of the present invention is to obviate these disadvantages and more particularly make it possible to obtain three-dimensional images of an object, on the basis of radiation emitted by the tracer contained in the object. Whilst taking account of the attenuation of radiation in said object or organ, as well as the geometry of the radiation detectors, the invention ensures a rapid convergence of the results of correctional processing of digital data, corresponding to the signals supplied by the detection zones of the radiation detector. It also makes it possible to carry out quantitative studies relating e.g. to the absorption of radiation emitted by elementary cells of the object or organ, for different sectional planes, the three-dimensional images being in fact images obtained in different sectional planes perpendicular to the detector plane.

The present invention therefore specifically relates to a process for obtaining three-dimensional images of an object from radiation emitted by a tracer contained in said object, said radiation being received by certain detection areas of a planar detector, designated by numbers n in the plane of said detector, the latter performing a rotary movement around the object, so that it constantly remains tangential to an imaginary cylinder of revolution (C), whose axis corresponds to an axis of the object, the angular positions of the planar detector being designated by angles $\theta_p$ between a reference plane (PR) passing through the axis of the object and a plane passing through the axis of the object and perpendicular to the plane of the detector, the object being assumed as broken down into elementary cells for the emission of radiation designated by their coordinates in a fixed reference mark (i, j, k), axis k of said mark being parallel to the axis of the object, the radiation received by certain detection areas being those which are emitted by the elementary cells of the object in a direction perpendicular to the plane of the detector, the detection areas supplying, for each angular position $\theta_p$, electrical signals whose amplitudes have values dependent on the intensities of the radiation received, said amplitude values being stored in order to obtain the images of the object, in the sectional planes, of ordinates k perpendicular to the axis of the object, wherein, for obtaining images of the object in the sectional planes, it comprises:

producing on the basis of the stored amplitude values, for each sectional plane of ordinates k, for all the angular positions $\theta_p$, and for all the detection areas of number n receiving the radiation, correction values of said amplitude values, whereby these correction values are obtained on initialization, on the basis of simulated amplitude values, corresponding to a simulated image of the object in which it is assumed that the distribution of the tracer is uniform, and from stored correction factors relating to the attenuation ($\mu$) of the radiation in the object, as a function of coordinates (i, j) of each elementary cell and relating to the geometry of each detector;

determining and storing for each sectional plane, for all the angular positions ($\theta_p$) and for all the detection areas of numbers n which receive the radiation, the values of the respective differences between the values of the amplitudes of the signals supplied by these areas and the correction values, the images corresponding to the values of the amplitudes of the signals supplied by the detection areas being available for the sectional planes for which the values of the differences comply with a predetermined convergence criterion, then, when the values of the differences do not comply with the predetermined criterion, the process then comprises:

producing other correction values of the signal amplitude values, for the sectional planes of ordinates k, for all the angular positions $\theta_p$ and for all the detection areas of numbers n which receive the radiation, said other correction values being obtained from values of stored differences, on the basis of said correction factors and on the basis of stored filtering coefficients ($\lambda$) of said other correction values;

performing for each sectional plane of ordinates k, for all the angular positions ($\theta$p) and for all the detection areas receiving the radiation, additions between respectively the stored amplitude values and the other correction values, the values of the results of these additions being stored, in order to supply the corresponding images of the object in the sectional planes or ordinates k or to obtain new correction values on the basis of the results of said additions until these results converge.

According to another feature of the invention, the correction values are obtained for each sectional plane of ordinates k, for all the angular positions $\theta$p and for all the areas receiving radiation, by multiplication of the values of the simulated amplitudes or resulting from additions, with the correction factor values.

According to another feature of the invention, the other correction values are obtained for each sectional plane of ordinates k, for all the angular positions $\theta$p and for all the detection areas receiving the radiation, by multiplication of said differences with said correction factors and with said filtering coefficients.

According to another feature, the process consists, for each sectional plane of ordinates k, for all the angular positions $\theta$p to be determined and stored, prior to obtaining the correction values, of the coordinates (i, j) of a mask of the space external of the images of the desired sections, of determining the correspondences between the numbers of the detection areas n and the coordinates (i, j) of the elementary cells located in the mask and then comparing the numbers of the detection areas defined by the mask with the numbers of the detection areas receiving the radiation.

According to another feature, the process consists of using a microcomputer connected to at least one memory and to image display means, for controlling the rotation of the detector, the marking of the angular positions $\theta$p around the object, the markings of the detection areas and the coordinates i, j, k, and for carrying out all the operations of storing, correcting and displaying images.

The invention also relates to an apparatus for performing the present process, for obtaining three-dimensional images of an object on the basis of radiation emitted by a tracer contained in said object, comprising a planar detector having detection areas designated by numbers n and able to supply signals respectively dependent on the intensities of the radiation received in a direction perpendicular to the plane (P) of the detector, said detector performing a rotary movement around the object, so that it remains constantly tangential to an imaginary cylinder (C), whose axis corresponds to an axis of the object, means for controlling and marking the angular position ($\theta$p) of the detector, said positions being marked between a reference plane ($P_R$) passing through the axis of the object and a plane passing through the axis of the object and perpendicular to the plane of the detector, the object being fictitiously broken down into elementary cells for emitting the radiation and designated by their coordinates in a fixed reference marking (i, j, k), the axis k of said marking being parallel to the axis of the object, the radiation received by certain detection areas designated by their numbers n being those emitted by the elementary cells of the object in a direction perpendicular to the plane of the detector, the detection areas supplying, for each angular position $\theta$p, electrical signals whose amplitudes have values which are dependent on the intensities of the radiation received, said amplitude values making it possible to obtain images of the object in sectional planes of ordinates k, perpendicular to the axis of the object, wherein it comprises iterative processing means by convergence of the values of the amplitudes of the signals from the detection areas, which have received radiation, said processing means being connected to display means for displaying the images corresponding to each sectional plane of ordinates k after each iteration.

According to another feature of the invention, the processing means comprise:

storage means which, for all the ordinates k of the sectional planes and all the angular positions $\theta$p of the detector, make it possible to store:

the values of the amplitudes of the signals supplied by the detection areas of numbers n, which have received radiation, the coordinates (i, j) of the elementary cells which may have emitted radiation to said detection areas of numbers n, reference values of the signal amplitudes, said values being simulated or obtained at the end of a preceding processing operation by the device of signal values corresponding to the detection areas, correction factors to be applied to the reference values, at least one amplitude value filtering coefficient;

first means for multiplying the reference amplitude values by the correction factors, the values of the results of these multiplications being recorded by storage means;

means for comparing the signal amplitude values supplied by the detection areas with reference values, the values of the results of these differences being recorded in the storage means;

means for testing the convergence of the values of the differences, as a function of a predetermined convergence criterion, display means being connected to the testing means for displaying the images of the sectional planes of ordinates k, when the convergence criterion is respected;

second means for the multiplication of the values of the differences with the correction factors and the filtering coefficient, said means being used when the convergence criterion is not respected, the values of the results of these multiplications being recorded in the storage means;

means for the addition of the values of the multiplication results to the reference amplitude values, the testing means being connected to the display means for controlling the display of images of the sectional planes of ordinates k on the basis of the results of the additions, when a convergence criterion of the values of the addition results is respected, said addition means being connected to the first multiplication means and to the storage means, so that when the convergence criterion of the values of the results of the additions is not respected, the reference values supplied to said second multiplication means are values of the results of the additions.

According to another feature, the apparatus also comprises means for controlling the storage means so that the latter record, for each sectional plane ordinate k, and for all the angular positions $\theta p$, masking coordinates (i, j) defining a limiting contour for the reconstruction of the object, and means for comparing the masking coordinates with the coordinates (i, j) of the elementary cells which have emitted radiation, so that account is only taken of the detection areas, whose numbers n correspond to elementary cells located in the limiting masking content.

According to another feature, the correction factors recorded in the storage means relate to the geometry of the detection areas, at the solid angles under which are seen the detection areas receiving radiation, on the basis of corresponding elementary cells of the object, and to the attenuation of the radiation as a function of the distance separating an elementary cell from the masking contour.

Finally, according to another feature, the process and apparatus according to the invention are applied to the tomographic reconstruction of the three-dimensional images of an organ, into which has been injected a gamma radiation emitting tracer.

BRIEF DESCRIPTION OF THE DRAWINGS

The invention is described in greater detail hereinafter relative to non-limitative embodiments and with reference to the attached drawings, wherein show.

DETAILED DESCRIPTION OF THE PREFERRED EMBODIMENTS

Figure 1:
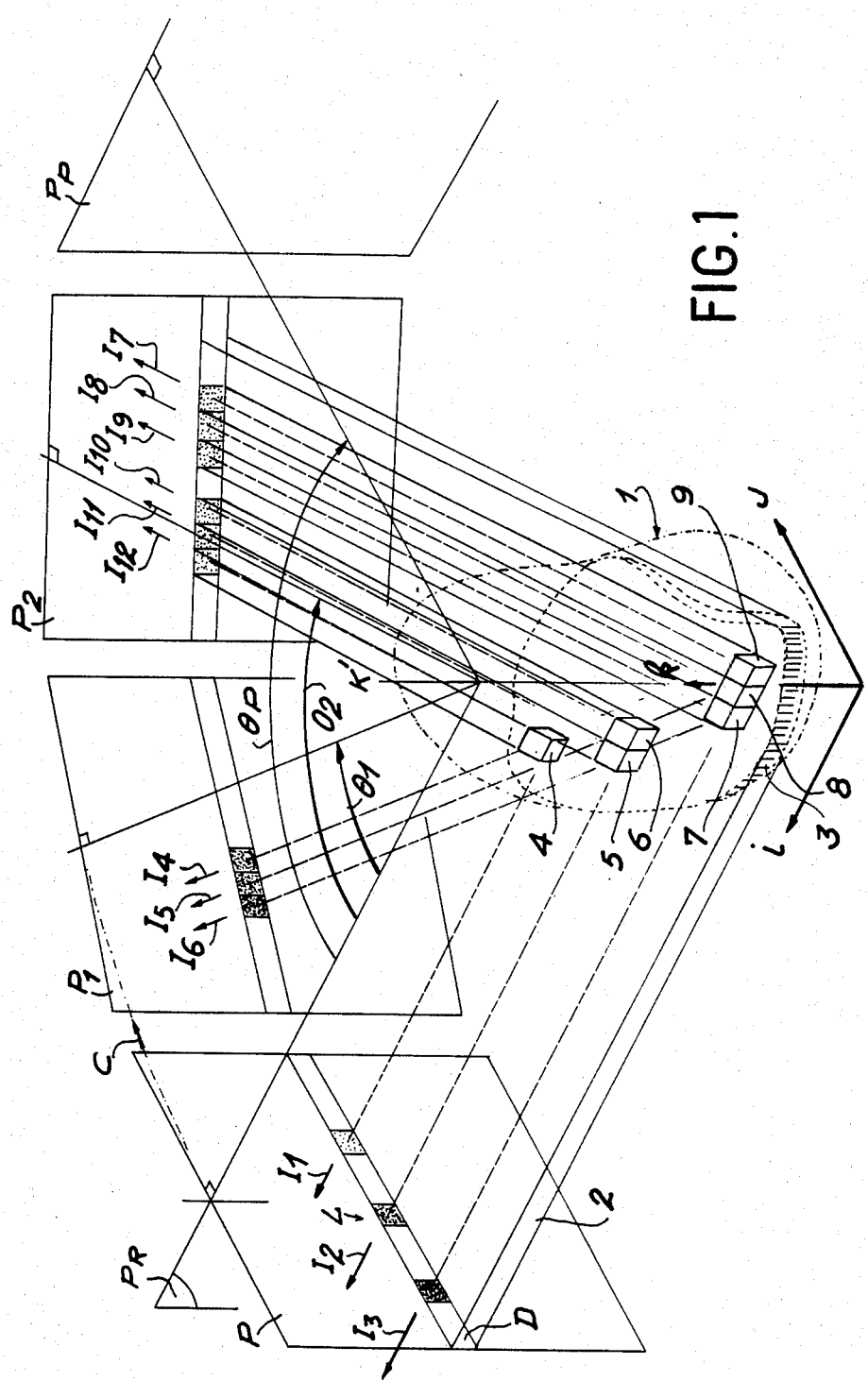
FIG. 1 provides a better understanding of the process according to the invention and diagrammatically shows the different angular positions of a planar radiation detector with respect to the organ or object to be examined.

FIG. 1 provides a better understanding of how the process according to the invention is performed. FIG. 1 shows an object or organ 1, whereof it is desired to obtain three-dimensional images, on the basis of radiation emitted by a tracer contained or injected into said object or organ. It is assumed that said radiation can be intercepted or trapped by detection areas D located in the plane P of a detector. Each of these detection areas only intercepts radiation received perpendicular to plane P, due to a collimator having channels perpendicular to said plane. The detection areas are designated in this plane by numbers n, which can be e.g. binary coded numbers, corresponding to the numbers of the lines and columns in which are located the considered detection areas. According to the process of the invention, plane P linked with the camera performs a rotary movement around a major axis KK' of the object to be examined, so that it remains constantly tangential to an imaginary cylinder of revolution C, whose axis corresponds to that of the object. The successive angular positions of this plane about object 1 are designated by angles $\theta_1, \theta_2 \ldots \theta_p$, measured between a reference plane PR and a plane passing through the axis of the object and perpendicular to the plane of the detector. Thus, in the embodiment shown in the drawing, the angular position of plane P relative to the reference plane PR is designated by O, whereas the following successive positions in which the plane P is represented in $P_1, P_2 \ldots P_p$ are designated by the angular positions $\theta_1, \theta_2 \ldots \theta_p$. The object is assumed to be fictitiously broken down into elementary cells for the emission of radiation designated by their coordinates, in a fixed reference marking (i, j, k) whose axis k is parallel to the major axis KK' of the organ or object. The radiation received by the detector is emitted by elementary cells of the object in a direction perpendicular to plane P of the detector. In order to simplify representation, the drawing diagrammatically shows certain of the elementary cells 4, 5, 6, 7, 8, 9 contained in a section 2 of the object or organ. For example, this section corresponds to portion 3 of the object or organ, contained in two parallel sectional planes, which are perpendicular on the one hand to the detector plane P, and on the other hand to the axis KK' of the organ. Marking i, j, k makes it possible to mark the ordinates k of sections perpendicular to KK'.

The detection areas D located at the intersection of plane 2 with the detector plane P are diagrammatically shown. Only certain of the elementary cells 4, 5, 6, 7, 8, 9 located in section 3 and emitting e.g. gamma radiation in the direction of line L of detection area D are shown, but it is obvious that other elementary cells are also present. In order to facilitate the understanding of the drawing, the other sections of the organ or object 1, parallel to the section 2 and intervening in the process are not shown, said sections having other ordinates k. In the case where the radiation-emitting elementary cells 4 to 9 are arranged in the represented manner and plane P occupies the position O relative to plane PR, detection areas having given numbers n supply signals $I_1, I_2, I_3$, whose amplitudes respectively correspond to the contributions of the radiation intensities supplied by elementary cell 4, the group of elementary cells 5, 6 and the group of elementary cells 7 to 9. When plane P has rotated around the organ or object 1 to occupy the angular position $P_1$ designated by $\theta_1$, other detection areas carrying given numbers n and belonging to the same line of detection areas supply electrical signals $I_4$, $I_5$, $I_6$, whose amplitudes respectively consist of the contributions of the intensities or the sum of the intensities of radiation emitted by the group of elementary cells 4 and 9, the group of elementary cells 6 and 8 and the group of elementary cells 5 and 7. The same would apply on further rotating plane P about organ 1, so that it occupies the angular position $P_2$, designated by $\theta_2$. Here again, detection areas which also carry given numbers n and belonging to the same detection line as hereinbefore supply signals $I_6$, $I_7$, $I_{11}$, whose amplitudes respectively incorporate contributions to the intensities of radiation emitted by elementary cells 4 to 9. The same reasoning applies to radiation emitted by elementary cells belonging to other sectional planes of ordinates k, parallel to sectional plane 2 and not shown in the drawing. As will be shown hereinafter, the numbers of the detection areas which have supplied signals for each angular position $\theta_p$ of the detection plane about organ 1 are recorded in the memory. These numbers are associated, as will be shown hereinafter, with the coordinates i, j, k of the elementary cells, which have supplied radiation in the direction of the detector. The amplitudes of the signals supplied by certain detection areas are also coded in accordance with their values.

Figure 2A:
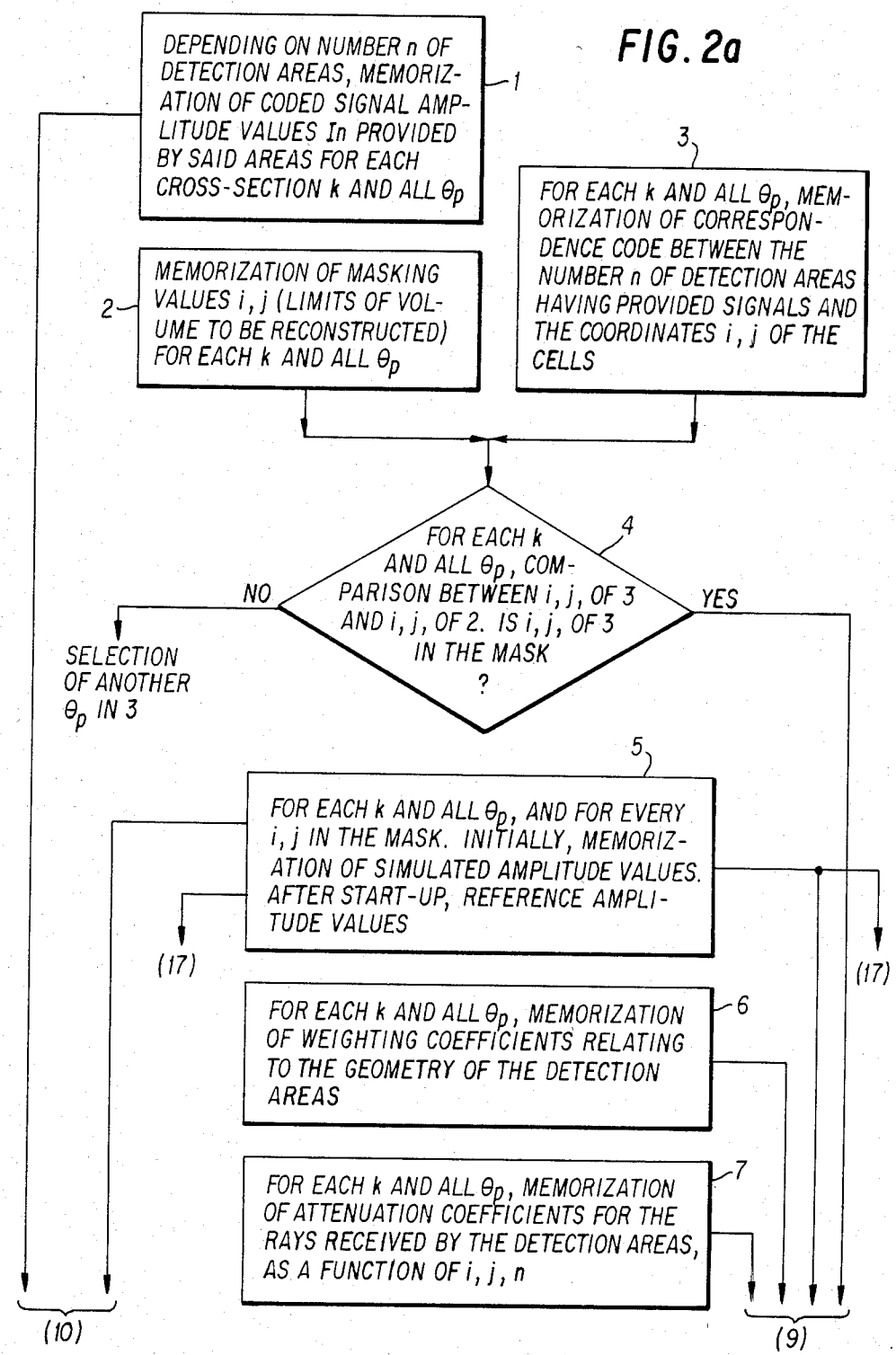
FIGS. 2a, 2b and 2c a flowchart showing the different operations involved in the process according to the invention.
Figure 2B:
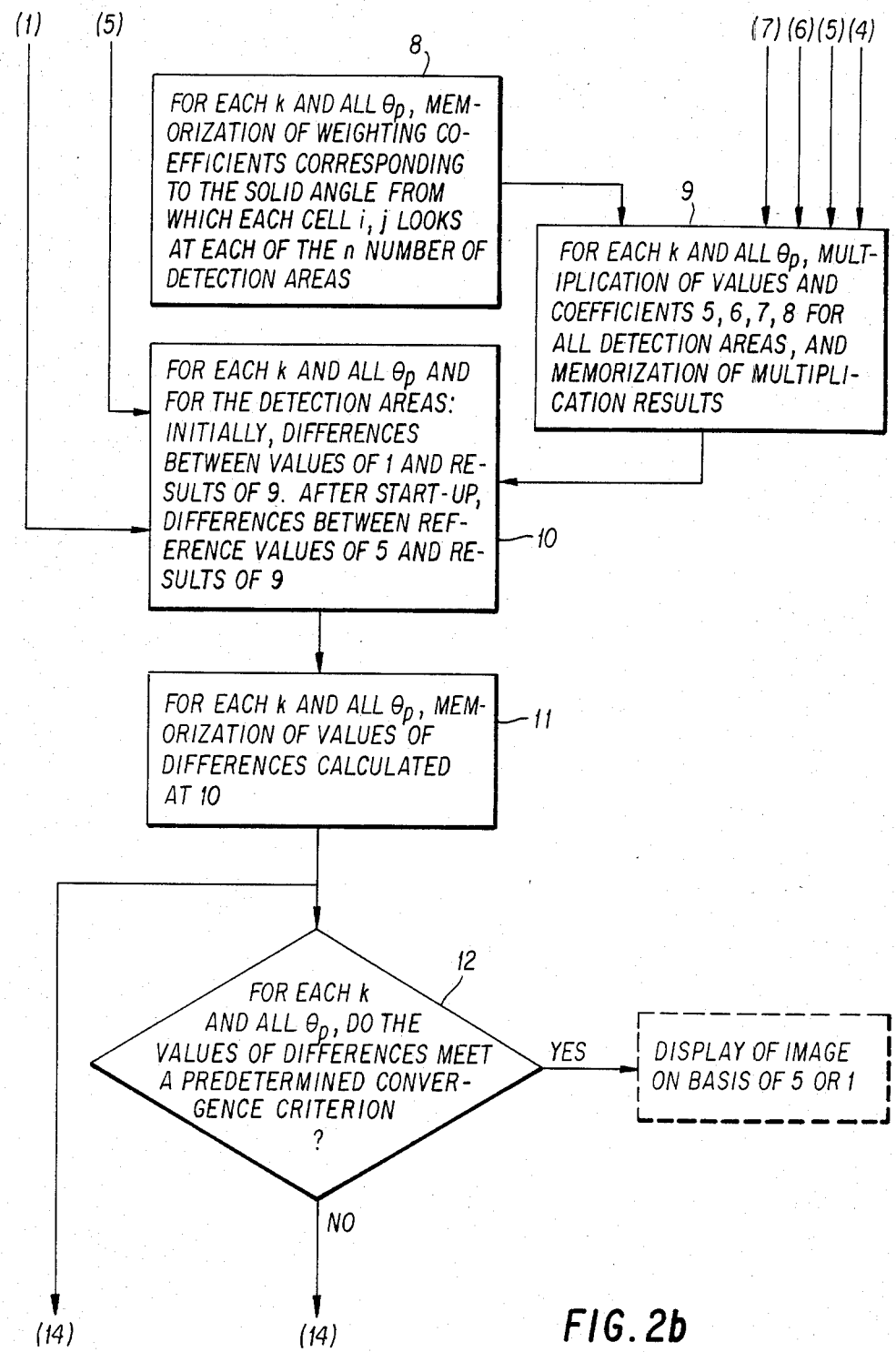

FIGS. 2a and 2b show a flowchart providing a better understanding of the performance of the process according to the invention. This flowchart represents the different stages of the process, designated by the numbers.

According to the process of the invention and the stage indicated at 1, storage takes place of the coded values of the amplitudes of signals $I_1$, $I_2$, ... $I_n$ supplied by the elementary detection areas of the detector which have received radiation, for each value of the ordinates k of the sectional planes and for all the angular positions $\theta_p$ of the plane of the detector about organ 1. These amplitude values are obviously associated with the numbers n of the detection areas which have received radiation, for all the sections of ordinates k parallel to section 2 in FIG. 1. It is assumed throughout the remainder of the description that all the processing operations are performed for each value of k, the different values of the angular positions $\theta p$ being successively scanned for a given value of ordinate k of the section, before passing to another value of k.

Then, as indicated at 2, for each value of k and all the positions $\theta p$, storage takes place of masking values relating to the limiting coordinates i, j of the volume of the organ or object, whose image is to be reconstructed.

The following operation 3 consists of storing, for each ordinate k of the sectional plane and for all the angular positions $\theta p$, the correspondence code between numbers n of the detection area which have supplied signals $I_n$ and the coordinates i, j of the elementary cells which are liable to have emitted radiation towards certain detection areas, in a direction perpendicular to their plane.

The following operation 4 consists, for each value of k and for all the angular positions $\theta p$, comparing the coordinates i, j of the elementary cells which have emitted radiation and which are marked at the end of operation 3, with masking coordinates i, j defined in operation 2. Thus, operation 4 consists of masking whether the elementary cells liable to have emitted radiation in the direction of certain detection areas (such as defined in operation 3) are located within the volume defined by the masking coordinates. If the answer to this question is negative (NO), another angular position $\theta_p$ of the plane of the detector is selected and the aforementioned comparison is carried out for other values of coordinates i, j. However, if the answer to the question asked in 4 is affirmative (YES), operation 9 is carried out.

Prior to operation 9, it is necessary to carry out other storage operations 5, 6, 7, 8 on the basis of coded values of amplitudes of reference signals liable to be supplied by the detection areas, for all the coordinates i, j of the elementary cells of the object or organ. On initialization, it is assumed that these reference values are simulated corresponding to a uniform distribution of the tracer in the object. Following this initialization, and as will be shown hereinafter, these reference values result from a preceding iterative processing of amplitude values.

Figure 2C:
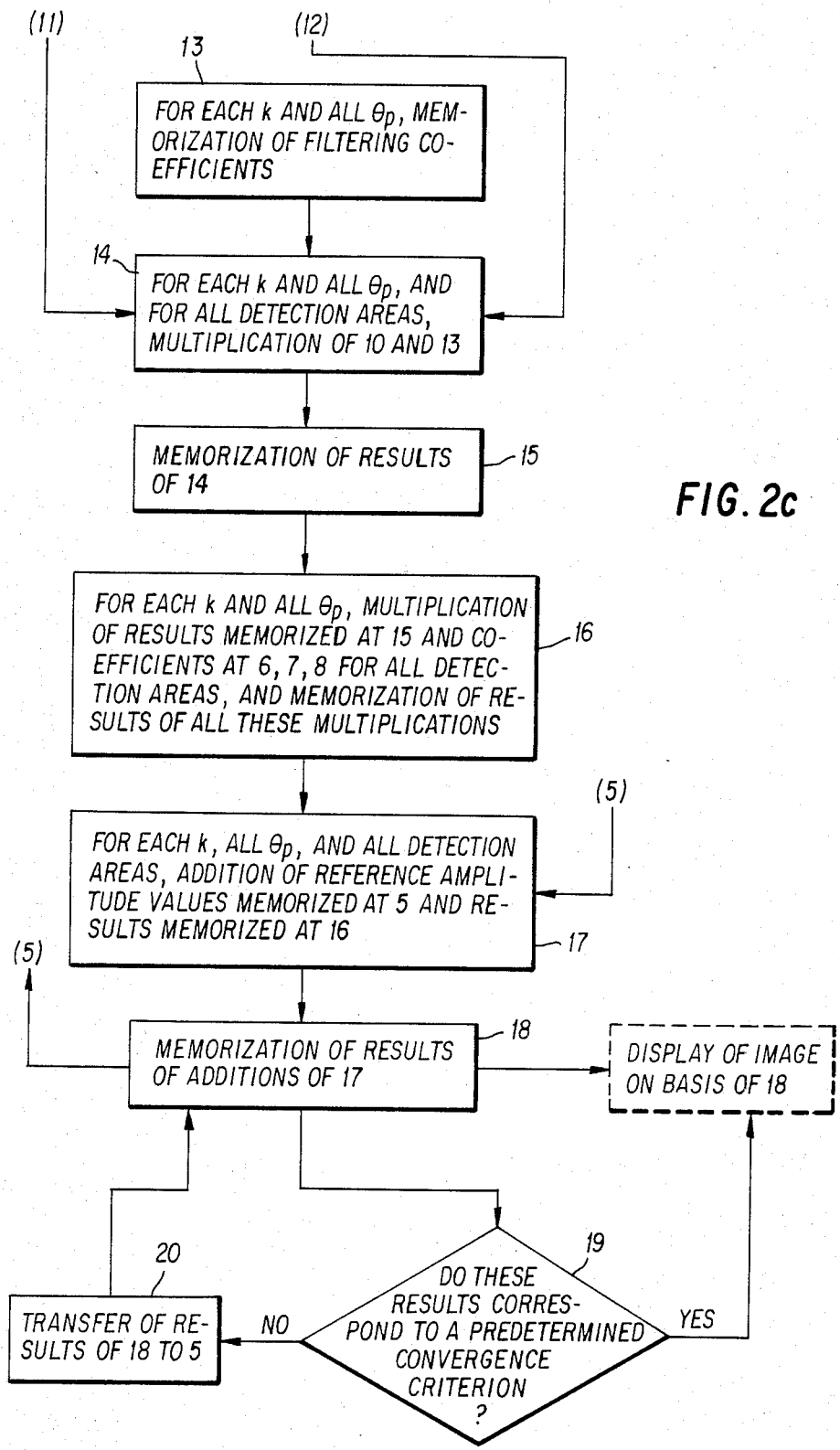
Figure 4:
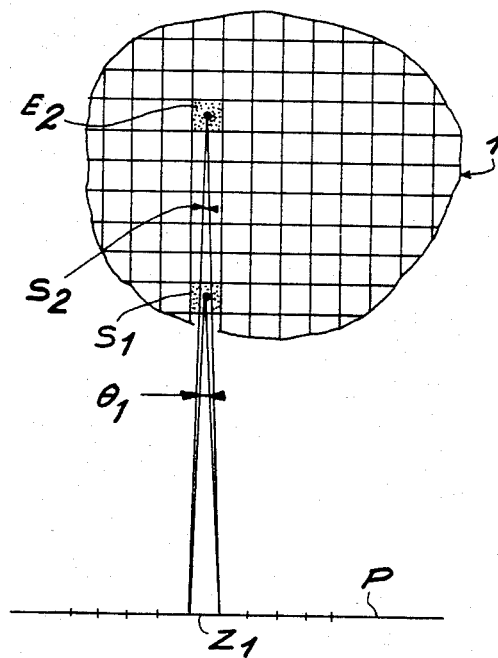
FIG. 4 illustrates the influence of the solid angle under which a detection area is seen from an elementary cell of the organ.

Operation 6 consists of storing for all the detection areas, weighting factors to be applied to the amplitudes of the signals supplied by these areas. These weighting factors take account of the realtive positions of the detection areas and of the elementary cells of the organ or object. Thus, as has been shown in connection with FIG. 2, for a given section of the organ or object 1, the elementary cell E emits radiation, which is detected by a single detection area $Z_1$, for a position P of the detector plane. For another position $P_1$ of the detector plane, said same cell emits radiation, which is detected not only by a detection area $Z_3$, but also by two adjacent areas $Z_2$ and $Z_4$. The weighting factors of operation 6 make it possible to make corrections to the processing operations of the signals from the detection areas, in order to take account of the relative positions of the cells and the detection areas.

For each ordinate k and for all the angular positions $\theta_p$ of the detection plane, operation 7 consists of storing the attenuation coefficients $\rho$ of the radiation received by the detection areas, as a function of the numbers n of said areas and the coordinates i, j of the elementary cells able to emit radiation in the direction of these detection areas. Thus, these attenuation coefficients are linked with the distance separating an elementary cell from the boundary of the organ, in a direction perpendicular to the plane of the detector. Thus, the further an elementary cell is positioned from the boundary of the organ and the higher the attenuation of the radiation which it emits, which is due to the following points.

In order to obtain precise quantitative data in gamma photon emission tomography, it is necessary to take account of the autoabsorption of photons in the traversed tissues. The data to be extracted are the volume of an organ or cavity, the size of a lesion, etc.

Autoabsorption is an important source of deterioration to the data. It is a non-linear effect, for which the generally proposed corrections of the first order are not valid on considering extensive radioactive distributions with a nonuniform attenuation (heart, liver, lungs, etc.).

In the present invention, a novel analytical approach is proposed for the three-dimensional restoration of images. This problem of three dimensions is reduced to a problem of two dimensions. The reconstruction of a region transverse to the axis of the object or organ, on the basis of projections, passes via the solution of an integral equation which mathematically expresses this problem. This integral is of form:

$$S(\vec{r}) = \int\int \frac{\rho(\vec{r'})}{|\vec{r}-\vec{r'}|} (ch_{|\vec{r}-\vec{r'}|}\mu d\rho) d\vec{r'}$$

in which $S(\vec{r})$ is a function determined on the basis of measured projections and $\rho(\vec{r})$ is the radioactive concentration whose determination is being attempted. It is a Fredholm's integral equation of the first kind, which can be written in symbolic form:

$$S(\vec{r})=O_{att}.\rho(\vec{r})$$

in which $O_{att}$ is a "tomographic operator" taking account of the effect of photon attenuation in the tissues. Such a formulation makes it possible to introduce a group of tomographic operators, taking account of the different effects linked with the physical response of the detection system. These operators can be expressed in the form of symmetrical linear operators for which a regularizing iterative solution can be proposed. It can be demonstrated that an iterative solution:

$$\rho_n.\vec{r}=\rho_{n-1}.\vec{r}+\lambda(S(\vec{r})-O_{att}\rho_{n-1}(\vec{r}))$$

is an analytical solution of the problem raised, in which $\lambda$ is a relaxation factor corresponding to a minimum standard. This factor is calculated in such a way as to manage the convergence and the regularizing effect on the final solution.

This method can be called a regularizing iterative method (RIM). The value of $\lambda$ in a first stage can be taken as equal to a constant, but in a second stage could be a matrix. This appropriately chosen value permits a rapid convergence (3 to 5 iterations) and, for this small number of iterations, is associated with noise filtering in the final solution (this filtering will be described hereinafter).

This very general formulation of the problem making it possible to find an accurate solution and filtered in a small number of iterations, whilst taking account of an attenuation of the photons possibly distributed in the considered range, is novel compared with already proposed reconstruction methods which are either empirical, or based on restrictive hypotheses (convex range and constant attenuation). Such a method is used in the present invention.

Operation 8 consists, for each value of k and all the angular positions $\theta p$, of storing the weighting factors relating to the solid angles under which each elementary cell of the volume to be reconstructed sees each detection area of rank n, as a function of the coordinates i, j of each of these elementary cells.

Figure 3:
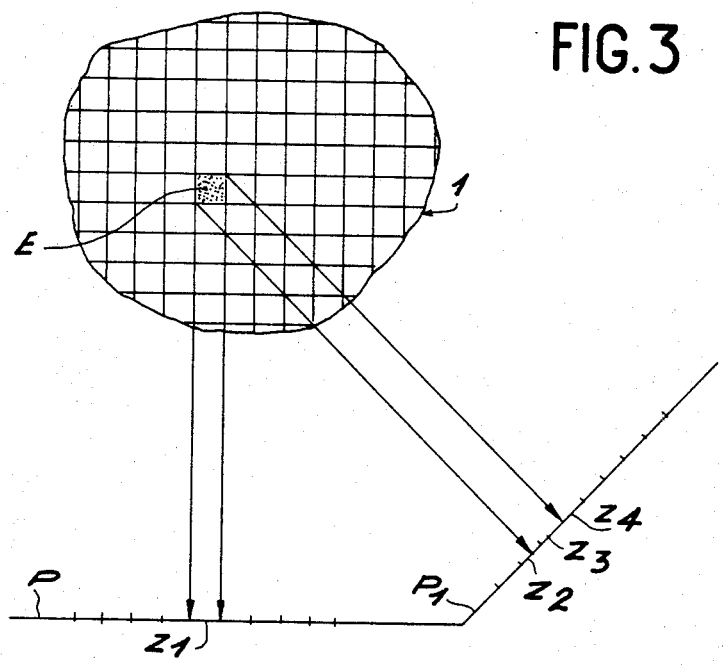
FIG. 3 illustrates the influence of the geometry of the detection areas of the detector, as a function of the angular position thereof relative to the organ.

As is shown in FIG. 3, the solid angle ($S_1$) under which the detection area $Z_1$ is seen from the elementary cell $E_1$ of the organ, is not the same as the angle $S_2$, under which the detection area $Z_1$ is seen from cell $E_2$. It is therefore necessary to take account of this correction, during the processing of the signals from the detectors.

The aforementioned multiplication operation 9 consists, for each value k and for all the angular positions $\theta_p$, multiplying the values of the coefficients stored at 6, 7, 8, which can be termed correction factors, with the reference values defined in 5. The results of the multiplication processes are stored and constitute, in the manner to be shown hereinafter, values for correcting the amplitudes of the signals $I_n$ from the detection areas and stored in 1.

Operation 10 consists of calculating, for each value of k, for all the angular positions $\theta_p$ and for all the detection areas of rank n which have supplied signals, the differences between the values of the amplitudes stored in 1 and the values of the results of the multiplications stored in 9. The results of the differences calculated at the end of operation 10 are stored as a result of operation 11, for each value of k and for all the angular positions $\theta_p$.

Operation 12 consists of investigating, for each value of k and all the angular positions $\theta_p$, whether the values of the differences stored in 11 comply with a stopping or convergence criterion of the process, which can be e.g. the fact that these values or differences are below or above predetermined values. If these differences are below these predetermined values or if they correspond to another stopping criterion (answer YES to question 12), it is possible to display the image of the object or organ, for one or more sectional planes of ordinates k, on the basis of the values of amplitudes stored in 1 on initialization, or in 5 after initialization.

However, if the answer to the question asked in 12 is NO, i.e. the values of the differences do not comply with this stopping criterion and are e.g. above the given values, it is not possible to directly display the image on the basis of the values of amplitudes stored in 1, or reference amplitudes stored in 5 at the end of a processing operation, without applying other correction values to said amplitudes.

Operation 13 is an operation in which, for each value of k and for all the angular positions $\theta_p$, storage has taken place of the filtering coefficients $\lambda$ to be applied to the values of the differences stored in 11, in order to ensure a rapid convergence of the processing operations of the signals and in order to filter the noise in consequence of these operations. These filtering coefficients are obtained on mathematical phantoms and are described hereinbefore.

Operation 14 consists of multiplying, for each value of k and for all the angular positions $\theta_p$ the result of each difference stored in 11 and each filtering coefficient stored in 13 for all the detection areas of rank n.

Operation 15 consists of storing the results of multiplications resulting from operation 14.

Operation 16 consists, for each value of k and for all the angular positions $\theta_p$, storing the results of the multiplication stored in 15, with the weighting and attenuation coefficients stored in 6, 7, 8, for each detection area of rank n. This operation also consists of storing the results of the last multiplications performed.

Operating 17 consists, for each value of k, for all the angular positions $\theta_p$ and for all the detection areas, of adding the reference values stored in 5 and the results of the multiplications stored in 16.

Finally, operation 18 consists of storing the results of the additions performed in 17. Following this storage operation, it is possible to display the image of the organ or object for one or more sectional planes of ordinates k, if the values stored in 18 comply with a predetrmined convergence criterion (answer YES to question 19). However, if this convergence is not obtained (answer NO to question 19), the results stored in 18 undergo multiplication operations 9, which involve the transfer of the results of 18 to 5, in accordance with the operation designated 20 in the drawing. The same operations as those described hereinbefore are then performed, starting at operation 9, until the convergence of the results is obtained in 18. Thus, this involves iterative processing in which the values being processed are those which would have permitted the display of a preceding imperfect image for each sectional plane.

It is obvious that the displays of images corresponding to the different sectional planes of ordinates k can be performed when all the processing operations of the signals have been carried for all these sectional planes. It is also obvious that the storage operations performed at 6, 7, 8, 13 are carried out on initialising the process.

Figure 5:
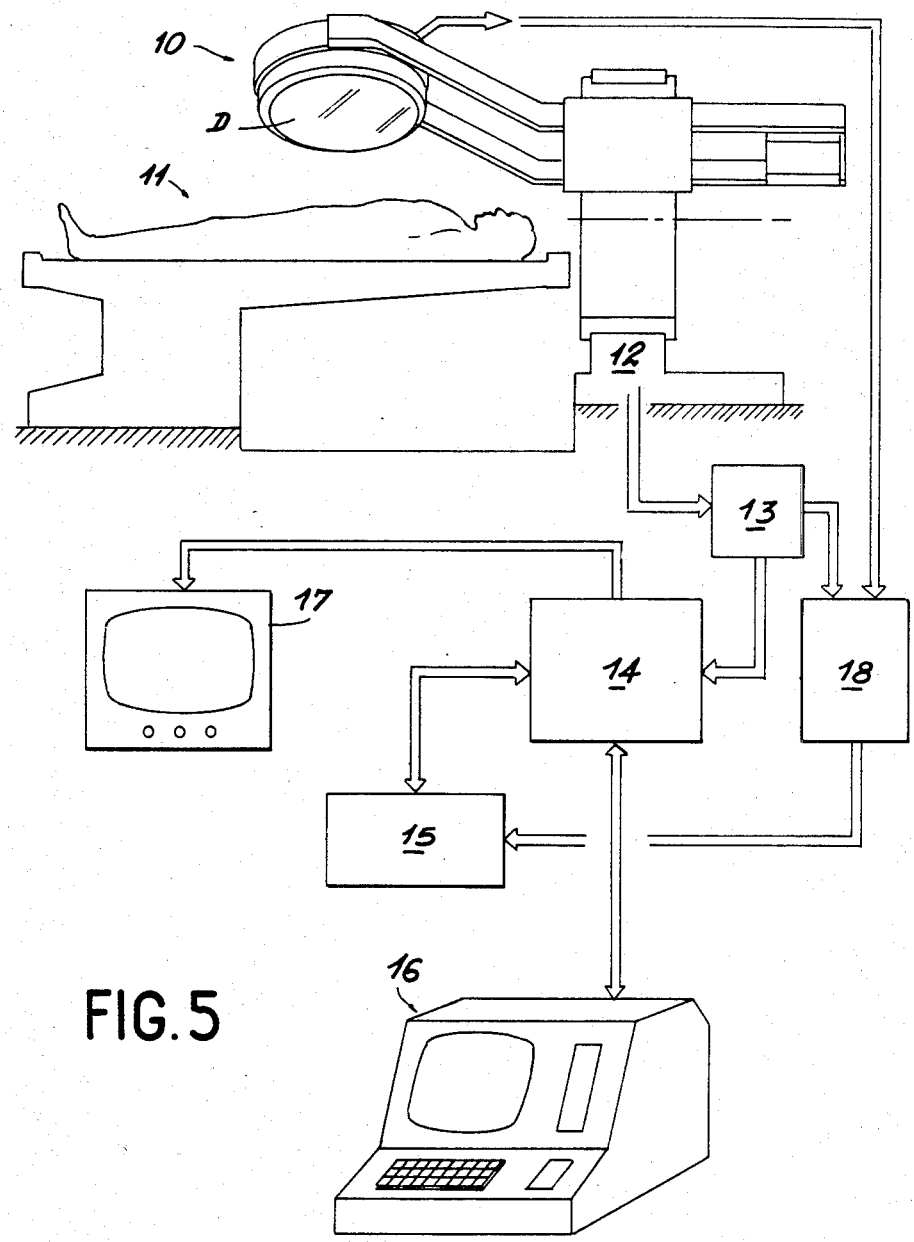
FIG. 5 a diagram of a tomographic assembly, comprising an apparatus making it possible to perform the process according to the invention.

FIG. 5 diagrammatically shows an apparatus for performing the process according to the invention. This apparatus comprises a planar detector D, which can e.g. be a gamma radiation detector, in a scintillation camera 10. The detected gamma radiation is emitted by elementary cells of an organ of a patient 11 to be examined. The patient is located on a table which can be adjusted in height and in two horizontal directions, whilst the detector can be rotated around the patient by rotary drive mean 12, which are not shown in detail here. Control means 13 make it possible on the one hand to control the said rotation and on the other to mark the rotation angles of detector D, relative to a reference plane not shown here. The angular positions of the detector, as well as the amplitude values of the signals, designated as a function of the numbers n of the detection areas are supplied by a coding means 18, in such a way that these amplitude values are recorded so as to correspond with each angular position and each detection area number. The different storage operations involved in the process according to the invention are performed in memory 15, associated with a microcomputer 14. The microcomputer in the apparatus according to the invention makes it possible to perform the aforementioned subtractions, additions and multiplications. The various instructions necessary for the operation of the microcomputer 14 can be introduced into memory 15, via microcomputer 14, by means of a control keyboard 16. It is obvious that memory 15 can in part be a read-only memory containing microinstructions, together with the values of the various coefficients and factors referred to hereinbefore. Finally, the display of the images corresponding to the different sectional planes of ordinates k takes place on a polychromatic display means 17.

It is obvious that this display only takes place when the processing of the signals takes place following a rotation of 360° around the patient of the plane of the detector.

Figure 6:
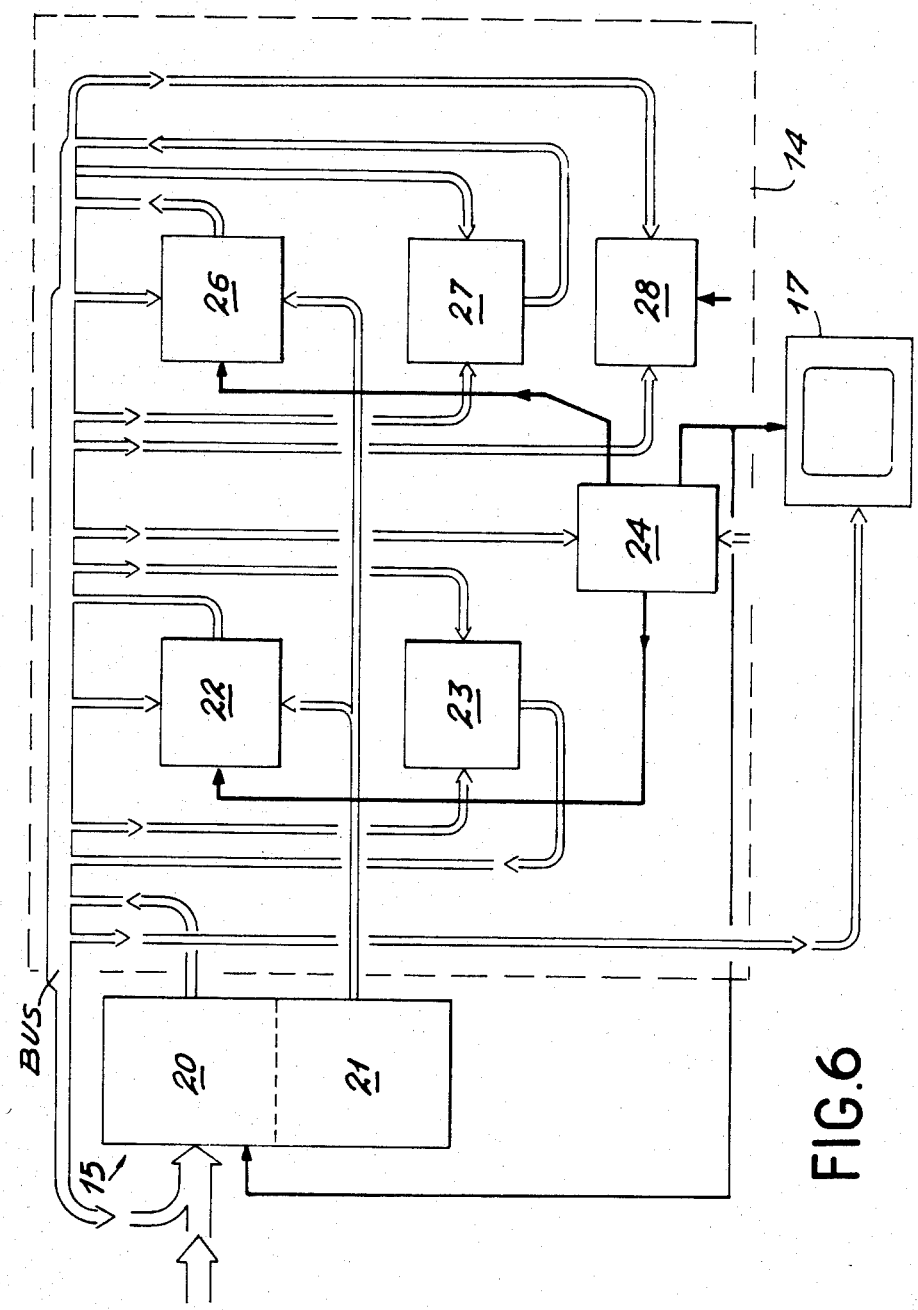
FIG. 6 a diagram showing in a more detailed form, the processing means used in the apparatus according to the invention.

The storage means constituted by memory 15 associated with microcomputer 14, constitute the iterative processing means used in the apparatus according to the invention. These means will now be described in detail relative to FIG. 6.

The storage means 15 comprise a memory, which can have a random access part 20 making it possible to record evolving data and a read-only part 21 making it possible to record non-evolving data, such as the aforementioned correction and filtering coefficients. They relate to the geometry of the detection areas, to the solid angles under which are seen the detection areas receiving the radiation from the corresponding elementary cells of objects, as well as the attenuation of radiation as a function of the distance separating an elementary cell from the masking contour. Finally, the read-only memory part also makes it possible to record the filtering coefficient $\lambda$ of the amplitude values. The random access part 20 of memory 15 is linked with the various components of microcomputer 14 by a bus. This random access part makes it possible to record, for all the ordinates k of the sectional planes and all the angular positions $\theta p$ of the detector, the following information:

the values of the amplitudes of the signals supplied by the detection areas of number n, which have received radiation;

the coordinates i, j of the elemenrary cells of the object or organ liable to have emitted radiation towards the detection areas of number n, it being possible by an initial study to establish a correspondence, for each angular position $\theta p$ of the detector, between the number n of the detection areas and the coordinates i, j, k of the elementary cells liable to emit radiation towards these detection areas, in a direction perpendicular to the detector plane;

reference values for the amplitudes of the signals which, as indicated hereinbefore, are simulated on initialising the apparatus, or are obtained as a consequence of a preceding processing of the signal amplitude values supplied by the detection areas;

for each sectional plane of ordinates k, the coordinates i, j of the masking contour of the areas outside the image to be obtained.

Microcomputer 14 which, with memory 15, forms the processing means for the apparatus according to the invention, comprises first multiplication means 22 which, according to the process of the invention, make it possible to multiply the reference amplitude values recorded in part 20 of memory 15, with the correction factors recorded in the read-only part 21 thereof. The values of the results of these multiplications are then recorded in the random access part 20 of memory 15. This microcomputer also comprises means 23 permitting on initialization, the comparison of the values of the amplitudes of the signals supplied by the detection areas and which are recorded as a consequence of a complete rotation of the detector around the object, with the values of simulated amplitudes recorded in the memory. Following initialization, comparison takes place in the manner to be shown hereinafter, between the reference amplitude values resulting from a preceding processing operation, and the amplitude values resulting from a processing operation which is taking place (values of the results at the output of the multiplication means 22). The results of the multiplications are recorded in memory 15. According to the invention, testing means 24 make it possible to test the convergence of the values of the differences supplied by the comparison means 23 and recorded in the memory, as a function of a predetermined convergence criterion, which is translated by control signals applied to an input 25 of the testing means. The display means 17 are controlled by these testing means so that, when the convergence criterion of the values of the differences is respected, it is possible to display the images of the sectional planes of ordinates k, on the basis of reference amplitude values recorded in memory 15 and used for the calculation of said differences. The processing means also comprise second multiplication means 26 permitting, when the convergence criterion is not respected, to multiply the values of the differences recorded in memory 15, with the aforementioned correction factors, as well as with the filtering coefficient $\lambda$. These second multiplication means are controlled by testing means 24 and are used when the convergence criterion is not respected. The values of the results of the multiplications are recorded in the random access part 20 of memory 15. Addition means 27 then make it possible to add the values of the results of the multiplications recorded in the memory to the values of the reference amplitudes recorded in the memory and resulting from a preceding processing operation. Testing means 24 make it possible to control the display of images of the sections of ordinates k by display means 17, when a convergence criterion of the values of the results of the additions is respected. This display operation is carried out on the basis of the results of these additions. However, if the convergence criterion is not respected, the testing means 24 control the first multiplication means 32 in such a way that all the processing operations performed by means 22, 23, 24, 26, 27, 28 are identically reproduced. In this case, multiplication means 22 do not process the simulated amplitude values, as on initialization, and instead multiply the results of the additions which have been recorded by the aforementioned correction factors. The processing operation is repeated in an identical manner until convergence of the results is obtained, either on the basis of the differences calculated by comparison means 23, or on the basis of additions calculated by addition means 27. This more or less rapid convergence is dependent on the filtering coefficient $\lambda$.

Finally, and as has been stated hereinbefore, it is possible to record in the random access part 20 of memory 15, for each ordinate k of the sectional plane and for all the angular positions $\theta$p, the masking coordinates i, j defining in each sectional plane, the limiting display contour of the object in said sectional plane. The processing means then comprise supplementary comparison means 28, making it possible to compare the masking coordinates recorded in memory 15 with the coordinates i, j of the elementary cells which have emitted radiation, said coordinates being recorded in the memory. This comparator makes it possible to increment the addressing of the random access part of the memory 15, so as to only take into consideration the detection areas, whose numbers n correspond to elementary cells located within the limiting masking contour. When following a comparison, the coordinates i, j of the elementary cells which have received radiation, are not located within the limiting masking contour, comparator 28 makes it possible to obtain access to data useful for the processing operations and located at an address in the memory corresponding to the following angular position $\theta$p.

What is claimed is:

1. A process for obtaining three-dimensional images of an object from radiation emitted by a tracer contained in said object, said radiation being received by certain detection areas of a planar detector, designated by numbers n in the plane of said detector, the latter performing a rotary movement around the object, so that it constantly remains tangential to an imaginary cylinder of revolution (C), whose axis corresponds to an axis of the object, the angular positions of the planar detector being designated by angles $\theta_p$ between a reference plane (PR) passing through the axis of the object and a plane passing through the axis of the object and perpendicular to the plane of the detector, the object being assumed as broken down into elementary cells for the emission of radiation designated by their coordinates in a fixed reference mark (i, j, k), axis k of said mark being parallel to the axis of the object, the radiation received by certain detection areas being those which are emitted by the elementary cells of the object in a direction perpendicular to the plane of the detector, the detection areas supplying, for each angular position $\theta_p$, electrical signals whose amplitudes have values dependent on the intensities of the radiation received, said amplitude values being stored in order to obtain the images of the object, in the sectional planes, of ordinates k perpendicular to the axis of the object, wherein, for obtaining images of the object in the sectional planes, it comprises:

producing on the basis of the stored amplitude values, for each sectional plane of ordinates k, for all the angular positions $\theta_p$, and for all the detection areas of number n receiving the radiation, correction values of said amplitude values, whereby these correction values are obtained on initialization, on the basis of simulated amplitude values, corresponding to a simulated image of the object in which it is assumed that the distribution of the tracer is uniform, and from stored correction factors relating to the attenuation (u) of the radiation in the object, as a function of coordinates (i, j) of each elementary cell and relating to the geometry of each detector;

determining and storing for each sectional plane, for all the angular positions ($\theta_p$) and for all the detection areas of numbers n which receive the radiation, the values of the respective differences between the values of the amplitudes of the signals supplied by these areas and the correction values, the images corresponding to the values of the amplitudes of the signals supplied by the detection areas being available for the sectional planes for which the values of the differences comply with a predetermined convergence criterion, then, when the values of the differences do not comply with the predetermined criterion, the process then comprises:

producing other correction values of the signal amplitude values, for the sectional planes of ordinates k, for all the angular positions $\theta_p$ and for all the detection areas of numbers n which receive the radiation, said other correction values being obtained from values of stored differences, on the basis of said correction factors and on the basis of stored filtering coefficients ($\lambda$) of said other correction values;

performing for each sectional plane of ordinates k, for all the angular positions ($\theta$p) and for all the detection areas receiving the radiation, additions between respectively the stored amplitude values and the other correction values, the values of the results of these additions being stored, in order to supply the corresponding images of the object in the sectional planes or ordinates k or to obtain new correction values on the basis of the results of said additions until these results converge.

2. A process according to claim 1, wherein the correction values are obtained for each sectional plane of ordinates k, for all the angular positions $\theta$p and for all the areas receiving radiation, by multiplication of the values of the simulated amplitudes or resulting from additions, with the correction factor values.

3. A process according to claim 2, wherein the other correction values are obtained for each sectional plane of ordinates k, for all the angular positions $\theta$p and for all the detection areas receiving the radiation, by the multiplication of said differences with said correction factors and with said filtering coefficients.

4. A process according to claim 3, wherein it comprises, for each sectional plane of ordinates k, for all the angular positions θp to be determined and stored, prior to obtaining the correction values, of the coordinates (i, j) of a mask of the space external of the images of the desired sections, of determining the correspondences between the numbers of the detection areas n and the coordinates (i, j) of the elementary cells located in the mask and then comparing the numbers of the detection areas defined by the mask with the numbers of the detection areas receiving the radiation.

5. A process according to claim 4, wherein it comprises using a microcomputer connected to at least one memory and to image display means, for controlling the rotation of the detector, the marking of the angular positions θp around the object, the markings of the detection areas and the coordinates i, j, k and for carrying out all the operations of storing, correcting and displaying images.

6. An apparatus for obtaining three-dimensional images of an object on the basis of radiation emitted by a tracer contained in said object, comprising a planar detector having detection areas designated by numbers n and able to supply signals respectively dependent on the intensities of the radiation received in a direction perpendicular to the plane (P) of the detector, said detector performing a rotary movement around the object, so that it remains constantly tangential to an imaginary cylinder (C), whose axis corresponds to an axis of the object, means for controlling and marking the angular position (θp) of the detector, said positions being marked between a reference plane ($P_R$) passing through the axis of the object and a plane passing through the axis of the object and perpendicular to the plane of the detector, the object being fictitiously broken down into elementary cells for emitting the radiation and designated by their coordinates in a fixed reference marking (i, j, k), the axis k of said marking being parallel to the axis of the object, the radiation received by certain detection areas designated by their numbers n being those emitted by the elementary cells of the object in a direction perpendicular to the plane of the detector, the detection areas supplying, for each angular position θp, electrical signals whose amplitudes have values which are dependent on the intensities of the radiation received, said amplitude values making it possible to obtain images of the object in sectional planes of ordinates k, perpendicular to the axis of the object, wherein it comprises iterative processing means by convergence of the values of the amplitudes of the signals from the detection areas, which have received radiation, said processing means being connected to display means for displaying the images corresponding to each sectional plane of ordinates k after each iteration.

7. An apparatus according to claim 6, wherein the processing means comprise:
storage means which, for all the ordinates k of the sectional planes and all the angular positions θp of the detector, make it possible to store:
the values of the amplitudes of the signals supplied by the detection areas of numbers n, which have received radiation,
the coordinates (i, j) of the elementary cells which may have emitted radiation to said detection areas of numbers n,
reference values of the signal amplitudes, said values being simulated or obtained at the end of a preceding processing operation by the device of signal values corresponding to the detection areas,
correction values to be applied to the reference values,
at least one amplitude value filtering coefficient;
first means for multiplying the reference amplitude values by the correction factors, the values of the results of these multiplications being recorded by storage means;
means for comparing the signal amplitude values supplied by the detection areas with reference values, the values of the results of these differences being recorded in the storage means;
means for testing the convergence of the values of the differences, as a function of a predetermined convergence criterion, display means being connected to the testing means for displaying the images of the sectional planes of ordinates k, when the convergence criterion is respected;
second means for the multiplication of the values of the differences with the correction factors and the filtering coefficient, said means being used when the convergence criterion is not respected, the values of the results of these multiplications being recorded in the storage means;
means for the addition of the values of the multiplication results to the reference amplitude values, the testing means being connected to the display means for controlling the display of images of the sectional planes of ordinates k on the basis of the results of the additions, when a convergence criterion of the values of the addition results is respected, said addition means being connected to the first multiplication means and to the storage means, so that when the convergence criterion of the values of the results of the additions is not respected, the reference values supplied to said second multiplication means are values of the results of the additions.

8. An apparatus according to claim 7, wherein it also comprises means for controlling the storage means so that the latter record, for each sectional plane ordinate k, and for all the angular positions θp, masking coordinates (i, j) defining a limiting contour for the reconstruction of the object, and means for comparing the masking coordinates with the coordinates (i, j) of the elementary cells which have emitted radiation, so that account is only taken of the detection areas, whose numbers n correspond to elementary cells located in the limiting masking content.

9. An apparatus according to claim 8, wherein the correction factors recorded in the storage means relate to the geometry of the detection areas, at the solid angles under which are seen the detection areas receiving radiation, on the basis of corresponding elementary cells of the object, and to the attenuation of the radiation as a function of the distance separating an elementary cell from the masking contour.

* * * * *